United States Patent [19]

Fishman

[11] Patent Number: 5,769,901
[45] Date of Patent: Jun. 23, 1998

[54] POWDERED HAIR DYE COMPOSITION AND METHOD OF APPLICATION

[76] Inventor: Yoram Fishman, 3300 Wonderview Plaza, Los Angeles, Calif. 90068

[21] Appl. No.: 627,765

[22] Filed: Apr. 1, 1996

[51] Int. Cl.[6] ...................................................... A61K 7/13
[52] U.S. Cl. ........................ 8/406; 8/421; 8/424; 8/435; 8/524; 8/527
[58] Field of Search ............................... 8/405, 406, 421, 8/424, 431, 435, 498, 524, 527

[56] References Cited

U.S. PATENT DOCUMENTS

| | | | |
|---|---|---|---|
| 3,960,476 | 6/1976 | Ghilardi et al. | 8/524 |
| 3,981,676 | 9/1976 | Ghilardi et al. | 8/406 |
| 4,808,189 | 2/1989 | Oishi et al. | 8/408 |
| 4,834,768 | 5/1989 | Grollier | 8/405 |
| 4,895,575 | 1/1990 | Hocquaux et al. | 8/406 |
| 4,996,059 | 2/1991 | Grollier et al. | 8/405 |
| 5,053,051 | 10/1991 | Tennigkeit et al. | 8/406 |
| 5,116,388 | 5/1992 | Brooks | 8/406 |
| 5,118,323 | 6/1992 | Lim et al. | 8/405 |
| 5,131,912 | 7/1992 | Ehara et al. | 8/406 |
| 5,449,403 | 9/1995 | Andrean et al. | 8/406 |
| 5,560,750 | 10/1996 | Crews et al. | 8/435 |

FOREIGN PATENT DOCUMENTS

| | | |
|---|---|---|
| 3642097 | 6/1988 | Germany . |
| 57-18606 | 1/1982 | Japan . |
| 3-193723 | 8/1991 | Japan . |

OTHER PUBLICATIONS

English language translation of DE 3,642,097, Henkle, pp. 1–12, Jun. 1988.
Derwent Abstract of JP 1–175,925, Nakano Seiyaku, Jul. 1989.
Derwent Abstract of JP 51–148,043, Nippon Peroxide, Dec. 1976.
English language translation of JP 60–28912, Shiseido KK, Feb. 1985.
Charles Robins, Chemical and Physical Behaivior of Hair, ch. 6, pp. 171–195, 1988.

Primary Examiner—Paul Lieberman
Assistant Examiner—Caroline L. Dusheck
Attorney, Agent, or Firm—Alan S. Raynes

[57] ABSTRACT

A composition for a powdered hair dye includes an oxidative dye component, an oxidizing component and a thickening component. Other additives including protein derivatives and sucrose may also be utilized. The powdered dye composition may be placed into an applicator container so that the container is partially filled with the dye composition. Then when the user desires to use the dye, water is added to the container, the container shaken to mix the water and the powdered dye composition, and the mixture is then applied to the hair using an application mechanism which allows for easy and efficient application of the dye to the hair.

18 Claims, 3 Drawing Sheets

POWDERED HAIR DYE COMPOSITION AND METHOD OF APPLICATION

BACKGROUND OF THE INVENTION

1. Field of the Invention

This invention relates to a hair dye system, and more particularly to a powdered hair dye system providing improved hair appearance and convenient preparation and application to the hair.

2. The Related Art

Permanent hair dye systems have commonly been comprised of a combination of a dye material and a developer or activator solution, most commonly hydrogen peroxide. Additive materials including thickeners, fillers and perfumes are sometimes included in the hair dye system.

Typically, the two parts of the system are packaged separately until use, when they are combined in one container, the container capped, and then shaken well to mix and activate the product. The mixing container may be used as an applicator by, for example, snipping off the tip of the bottle and carefully pouring the mixed solution onto the roots of the hair and combing or working the solution into the hair by hand to thoroughly and completely saturate the hair. Gloves must be worn to avoid stains on the hands and fingers since the hands are used to spread and distribute the color. The mixture is usually left on the hair for about 15 to 30 minutes, depending upon the shade and color depth desired. Finally, the dye solution is shampooed out of the hair and the hair is dried.

The process may be repeated if the colorant is not evenly distributed or not of sufficient intensity. Care must be taken to prevent run offs onto clothing, furnishings, etc. Once the two solutions are mixed together, the mixture must be used within a relatively short time, such as within one hour.

Such a conventional system has a variety of shortcomings, including: (1) problems in mixing the components together; (2) the added time needed to prepare the working dye solution; (3) difficulty in controlling the liquid application while applying the dye to hair; (4) problems with applying the dye to hair on other parts of the body than head hair such as chest hair, underarm hair, mustache hair, etc.; (5) the harshness of the systems to the hair; (6) the additional processing steps, packaging, shipping expenses, and waste generated due to multiple containers.

It would be desirable to have a hair dye composition which is easy to use, fast to apply and provides even and controllable colors. It would also be desirable to utilize one or more additive materials which are inexpensive and would include materials to provide improved hair texture and appearance. In addition, it would be desirable to have a neat and efficient packaging method for the components containing hair dye, as well as convenient application of the hair dye to hair regardless of the location of the hair on the body. Embodiments of the present invention are directed toward these and other objectives.

SUMMARY OF THE DISCLOSURE

Embodiments of the present invention relate to a powdered hair dye including an oxidative dye component, an oxidizing component, and a thickening component. Other additives such as protein derivatives and sucrose may also be utilized. The oxidative dye component may be a material selected from the group consisting of aromatic phenols, polycyclic phenols, and hydroxy benzene with at least one substitute group. The oxidizing component may be a peroxide material such as sodium peroxy carbonate. The thickening component may be xanthan gum. The protein derivatives and sucrose both act to provide improved texture and even color development to the hair.

Other embodiments include methods for applying a hair dye to hair including the use of a bottle, wherein the bottle is partially filled with a powdered hair dye. When the user wants to apply the dye to the hair, water is added to the bottle, and the bottle is shaken so as to mix the contents and prepare a liquid dye composition for application to the hair. The bottle may include an applicator mechanism so that when the applicator mechanism is pressed against the hair, an appropriate amount of the liquid hair dye mixture travels through the applicator mechanism and is applied to the hair.

Embodiments of the invention may be mixed and then applied to the hair using the same container, thus eliminating the need for multiple containers and the associated waste, and shortening the clean up time. Furthermore, embodiments of the present hair dye system as described herein allow for safe, convenient application of the hair dye to the hair without the need for gloves and without the mess associated with conventional hair dye systems.

BRIEF DESCRIPTION OF THE DRAWINGS

Further objects, advantages and features of the present invention will become apparent from the detailed description, below, when read in conjunction with the accompanying drawings (which, for illustrative purposes, are not drawn to scale), which illustrate certain embodiments of the invention, where.

DETAILED DESCRIPTION OF PREFERRED EMBODIMENTS

Figure 1:
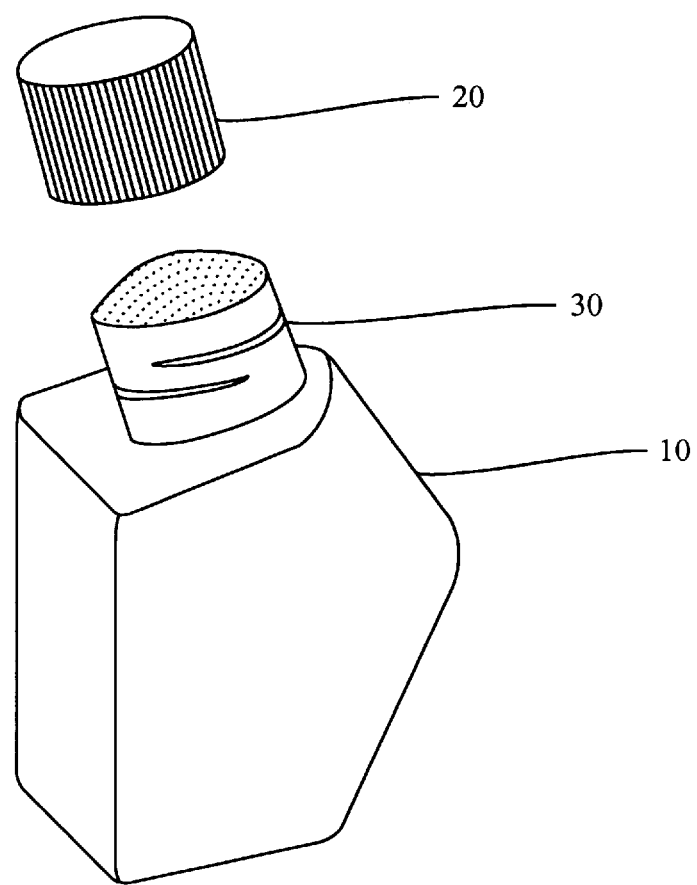
FIG. 1 shows a view of a bottle for holding and applying hair dye to hair, according to certain embodiments of the present invention.

Embodiments of the present invention relate to and include compositions for hair dyes including permanent hair dyes. Embodiments may include powdered compositions containing an oxidative dye, an oxidizing component, and additives including a thickening component and hair conditioning and nourishing components. Embodiments of the present invention may be utilized by adding a measured volume of water to the powdered composition within a container, placing an applicator onto the container, mixing the powder and water until the powder is dissolved in the water and the solution is at the proper working viscosity for application to the hair. Embodiments of the invention may be mixed and then applied to the hair using the same container.

Numerous oxidative dyes and dyeing agents may be used in embodiments of the present invention, including, for example, aromatic phenols, polycyclic phenols, hydroxy benzene with substitute groups (ortho, meta, para) such as nitro, amino, amido, sulfo, chloro, bromo, and combinations thereof. Examples include, but are not limited to: para phenylenediamine; para phenylenediamine hydrochloride; para phenylenediamine sulfate, meta phenylenediamine sulfate; ortho, meta, and para aminophenol; meta aminophenol sulfate; ortho, meta, and para nitrophenol;

2-nitrophenylenediamine; para amino ortho cresol; ortho, meta, and para chlorophenol; the acid salts of the above phenols; alpha naphthol; 1,4-dihydroxynaphthol; and resorcinol. Other oxidative dyes may also be used. In general, more water soluble oxidative dyes are preferred because they go into solution in a shorter time, such as under two minutes.

Numerous oxidizing agents may be used in embodiments of the present invention. For example, water soluble peroxides including sodium peroxycarbonate may be utilized. Other oxidizing agents which may be used include, for example, sodium perborate and urea peroxide. In general, oxidizing agents which are more water soluble are preferred because they go into solution faster.

Embodiments of the present invention may also include the use of sucrose or cane sugar as an additive and filler or diluent material. Sucrose provides several advantages. First, the sucrose is beneficial to hair, as it is hygroscopic and provides moisture to the hair, resulting in good hair texture and even color development. Second, sucrose assists the solubility of the powdered materials, including the dye, once the powdered materials are mixed with water. Third, sucrose is inexpensive. Fourth, food grade cane sugar is not toxic and is approved for cosmetic use by the FDA.

In another aspect, embodiments of the present invention may include the inclusion of soluble protein material. The protein may be partly or totally hydrolized and may be derived from keratin protein, collagen protein and amino acid hydrosolates. Previously, the use of protein derivatives in hair coloring formulations has been limited because of instabilities in the mixture with the high PH dye solution or the peroxide solution when considering commercial shelf life. The presence of protein and protein derivatives in powdered form is stable, as described in accordance with embodiments of the present invention, gives the hair an improved texture and feel and superior coverage of color. A preferred protein material is Crotein WKP (manufactured by Croda, Inc., Persipanny, N.J.), which may be included as a hydrolyzed keratin protein.

In another aspect of embodiments of the present invention, a thickener may be utilized to improve the working viscosity of the composition. The dye composition should have an appropriate thickness so that it is properly localized on the hair during application. Brookfield viscosity is most preferably in the range of about 50 to about 150 centipoises, when measured with a Brookfield LVT viscometer and using a No.2 spindle at 12 rpm. Preferred embodiments of the present invention utilize xanthan gum. Other thickeners which could be utilized include, for example, tragacanth, agar, vegetable thickeners, low viscosity cellulose derivative thickeners, acrylic polymers, polyvinyl alcohol, and others.

In another aspect of embodiments of the present invention, the ingredients are mixed together in the powdered form. One example of an embodiment includes 42.5 wt % sodium peroxycarbonate, 42.5 wt % sucrose (cane sugar), 3 wt % xanthan gum, 2 wt % of hydrolyzed protein (Crotein WKP), and 10 wt % dye material. Other embodiments include varying amounts of ingredients. The amount of dye material depends upon the shade desired. In certain embodiments, the powders are relatively uniform in size, for example, filtered through a screen of about 60 mesh Tyler and blended until reasonably uniform. Other powder particle sizes can be utilized, but in general, the smaller the particle size of the powder, the faster the powder will go into solution once it is mixed with water. In one preferred embodiment, the powders are mixed in a dry mixing cone or cylinder and then blended until uniform. Then the product may be metered into the appropriate container and sealed in a warm and dry environment to reduce humidity. A variety of containers may be utilized for holding the dry powder product. A preferred container capacity may be 2 liquid ounces, to which 12 grams of powdered product are added, leaving space for water in the container. The container material and design may be selected to be impervious to moisture and air, and may be at least somewhat transparent or translucent.

Figure 2:
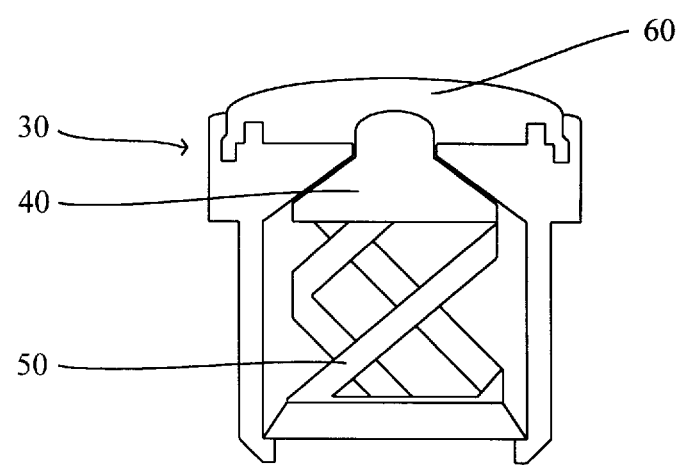
FIG. 2 shows a cross-sectional view of a dabber applicator according to certain embodiments of the present invention.

Embodiments of the present invention also relate to methods for applying a hair dye formulation to hair. In one preferred embodiment, the hair dye is placed into a bottle 10 having a sealing top 20 and a dabber applicator 30, as shown in FIG. 1. The powder only partially fills the bottle, and additional space in the bottle will be filled with water when the user is ready to prepare the dye composition for application to the hair. The sealing top 20 is used to seal the bottle 10 during storage. The dabber applicator 30 is used for applying the dye composition, after mixing with water, to the hair. The dabber applicator 30 allows for proper flow of the hair dye product for good coverage with controlled fluid movement advantages, and eliminates dripping problems, thus permitting hair dyeing without mess or streaking. As seen in FIG. 2, the dabber applicator 30 contains a valve stem 40 with an integral spring 50 for releasing the desired amount of product, and a foam or fabric material 60 through which the product flows and for contacting the surface of the hair. A variety of bottle and dabber applicator sizes and configurations may be utilized depending on factors such as the amount of product that will be used and the location on the body of the hair to be dyed.

Figure 3:
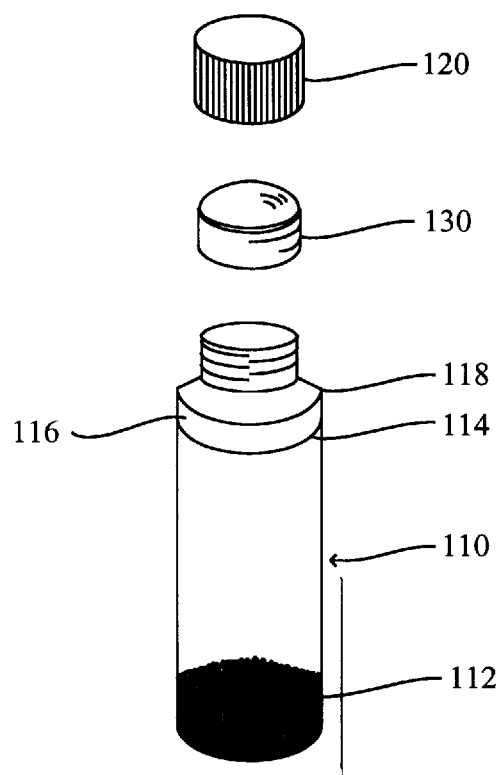
FIG. 3 shows a view of a bottle for holding and applying hair dye to hair according to certain embodiments of the present invention.

When the user is ready to apply the dye product to the hair, the sealing top may be removed and the appropriate amount of water added. For example, FIG. 3 shows an embodiment including a 2-ounce bottle 110 containing 12 grams of dye product 112. Water is added until the mark 114 near the shoulder 118 of the bottle 110 is reached, for a total weight of components in the bottle of about 60 grams, equivalent to 20% of activity. The water utilized may be simple tap water, and can be at tap temperature or at room temperature. Alternatively, the powder will dissolve faster if warm water (for example, 30°–35° C.) is used instead of room temperature or tap temperature water. If the temperature of the water used is too high, there may be problems with the mixture foaming upon mixing. A small amount of open volume 116 is left in the bottle 110 to facilitate proper mixing.

Sealing top 120 and/or dabber applicator 130 (similar to dabber applicator 30 shown in FIGS. 1 and 2) may be placed onto the bottle 110 after the water has been added and then the dye product and water are mixed by shaking the bottle 110. A small bead or marble could also be included in the bottle to promote mixing. Good results have been achieved when mixing is carried out for approximately 45 seconds to 2 minutes. In certain embodiments, good results have been obtained by allowing the mixed dye product to sit immediately after mixing, for a waiting period, for example, of approximately 1 to 2 minutes, so that the viscosity of the product can stabilize.

The bottle may be inverted at any convenient angle for application to the hair so that the dye solution can pass through the dabber applicator. The dye solution may be applied from the base of the hair upward, using circular strokes for even coverage. The dabber applicator allows for proper flow of the hair dye product for good coverage with controlled fluid movement advantages, eliminating dripping problems, thus permitting hair dyeing without mess or streaking. This system also eliminates the need for protective gloves normally worn when using conventional hair dye applicator bottles. After a soak and dye period of, for example, 5 to 15 minutes, the hair is thoroughly rinsed and shampooed. The application may be repeated for additional color density. Certain embodiments of the mixed dye product have been found to be effective for times up to approximately 2 hours after mixing with water.

Certain embodiments of the powdered dye composition of the present invention may include approximately 30–50 wt % of the oxidizing component, for example, sodium peroxicarbonate. More preferred embodiments include approximately 42–45 wt %. If the amount of the oxidizing component is too low, then the dye component may not fully react. If the amount of the oxidizing component is too high, then the dye component may become over reactive and not work properly on the hair, have a shorter shelf life, and be more unstable.

Certain embodiments of the powdered dye composition of the present invention also include a thickener, such as xanthan gum. Certain embodiments utilize approximately 1–4 wt % xanthan gum, with more preferred embodiments utilizing 2–3 wt % xanthan gum. If too little thickener is used, the product will be too thin. If too much thickener is used, then the product may become too thick and have problems with foaming and/or problems in delivery of the product to the hair. Embodiments of the present invention also may include sucrose and one or more oxidative dyes and dyeing agents or colorants, with the one or more hair dye materials preferably present in the range of approximately 4–13 wt %. Various hair dye agents may be mixed together, and the exact amount of hair dye mixture will depend on a variety of factors, including the hue, intensity, and covering power of each agent.

Embodiments of present invention provide superior dyeing results for both thick and thin hair, beards, mustaches, and other body hair such as chest hair. For example, conventional hair dyeing systems are difficult or impossible to apply to chest hair because the dye cannot be applied to the chest hairs without dripping and running all over and off of the chest. This may result in non-uniform dyeing and irritation of the skin. Embodiments of the present invention, having an appropriate viscosity and being applied, for example, through the dabber applicator, may be delivered to the hair in a controlled manner without fear of uncontrollable dripping, etc.

The quantity of sucrose in embodiments of the present invention may vary with the quantities of the other materials used. In certain embodiments the sucrose may be present in the range of approximately 30–65 wt %, and in certain preferred embodiments, approximately 42–48 wt %.

The quantity of water soluble proteins or their hydrosolates in the embodiments of the present invention may vary with the hair type and condition desired. In certain embodiments the protein may be present in a range of up to about 3 wt %. Certain preferred embodiments utilize about 1 to 2 wt % water soluble protein.

In addition, in certain embodiments, for application of the hair dye prod to the hair, good results have been obtained by mixing approximately 4–6 parts of water for each 1 part of powder in the bottle by weight. Certain preferred embodiments include 5 parts water for each 1 part of the powdered components.

In preferred embodiments, after the water has been added to the powdered hair dye product and the bottle shaken for approximately 30–60 seconds, the resulting product is a moderately basic solution having a pH of between about 8 and about 10.5, and having a viscosity of between about 50 and about 150 centipoises when measured with a Brookfield LVT viscometer and using a No. 2 spindle at 12 rpm.

Examples of hair dye compositions for achieving various colors according to the present invention include the following. Since there may be many modifications without departing form the scope of the invention, the examples below are not intended to limit the invention to the examples but to illustrate the invention more clearly.

Example 1

Light Neutral Brown Shade

| component | weight % |
| --- | --- |
| p-phenylenediamine | 5.0 |
| m-phenylenediamine sulfate | 1.0 |
| m-aminophenol | 2.0 |
| xanthan gum | 3.0 |
| sucrose | 45.0 |
| sodium peroxycarbonate | 44.0 |

Example 2

Medium Neutral Brown Shade

| component | weight % |
| --- | --- |
| p-phenylenediamine | 5.0 |
| m-aminophenol sulfate | 5.0 |
| xanthan gum | 3.0 |
| sucrose | 42.5 |
| Crotein WKP | 2.0 |
| sodium peroxycarbonate | 42.5 |

Example 3

Reddish Brown Shade

| component | weight % |
| --- | --- |
| p-phenylenediamine | 4.0 |
| 2-nitrophenylenediamine | 4.0 |
| xanthan gum | 2.5 |
| sucrose | 44.5 |
| sodium peroxycarbonate | 45.0 |

Example 4

Deep Reddish Brown Shade

| component | weight % |
| --- | --- |
| p-phenylenediamine | 4.0 |
| p-amino-o-cresol | 5.0 |
| Crotein HKP | 2.0 |
| xanthan gum | 2.5 |
| sucrose | 43.0 |
| sodium peroxycarbonate | 43.5 |

Example 5

Neutral Black

| component | weight % |
| --- | --- |
| p-phenylenediamine | 5.9 |
| m-aminophenol sulfate | 7.0 |
| m-phenylenediamine sulfate | 0.1 |
| xanthan gum | 3.0 |
| sucrose | 42.0 |
| sodium peroxycarbonate | 42.0 |

For the above compositions, the p-phenylenediamine, m-aminophenol sulfate, m-phenylenediamine sulfate, 2-nitro-p-phenylenediamine, p-amino-o-cresol, and maminophenol were obtained from Jos. H. Lowenstein & Sons, Brooklyn, N.Y.; the sodium peroxycarbonate was obtained from Browning Chemical Corp., White Plains, N.Y.; the xanthan gum had the trade name KELTROL CGF and was obtained from Calgon Corp., City of Industry, Calif.; the Crotein HKP was obtained from Croda, Inc., Persipanney, N.J.; and the granulated cane sugar was obtained as available as a food grade product from local suppliers as food grade cane sugar with a sieve size of greater than 60 mesh.

The components other than cane sugar were sieved through a 60 mesh U.S. stainless steel sieve. The components were mixed together and the mixed composition was placed into an applicator bottle so that the bottle was partially filled with the mixed composition. The applicator bottle was filled with tap water at room temperature and mixed. Mixing was carried out by hand by shaking the applicator bottle. The applicator bottles, bottle caps, and dabber applicator were obtained from Dab-O-Matic Corp., Mount Vernon, N.Y.

The examples were tested on previously untreated light grey and medium grey hair swatches, obtained from Alkinco (Alfred Klugmann, 264 West 40th St., N.Y.). Solutions of the hair color examples were spread over dry and untreated hair swatches and worked into the hair with a permanent waving brush. The dye example solutions were allowed to remain on the hair for a 3-minute time period. The swatches were then thoroughly washed and shampooed followed by blow drying. A set of swatches of each color was prepared, then tested for color fastness to sunlight, and durability to repeated shampoo and rinsing cycles.

The dyed hair swatches were washed with warm tap water and blown dry. The swatches were then cycled through a shampoo, rinse, and dry protocol at least ten times and then compared for fastness and evenness of coverage with control hair swatches. No difference was observed.

For Example 5 above, the following specific test results were obtained. The viscosity of the mixed solution after approximately 1 minute of mixing was 150 centipoise (measured using a Brookfield LVT Viscometer with a No. 2 spindle at 12 rpm). The pH of the mixed solution was 10.15. Direct sunlight exposure on light grey hair treated with the mixed solution produced no noticeable change within two weeks. There was some fading observed after three weeks of direct sunlight. The color fastness was observed to be similar to that of other hair dyes on the market. A series of ten wash and shampoo cycles did not show any indication of a color change. The other examples above showed similar results to those of Example 5.

The scope of the present invention is not limited to the specific embodiments discussed above. Other embodiments could include additional additives such as, for example, conditioning materials or surface-active agents. Furthermore, methods other than those described above may be used for applying dye compositions to the hair.

What is claimed is:

1. A powdered hair dye composition comprising:
   an oxidative dye component in powdered form in an amount effective for coloring hair;
   an oxidizing component in powdered form in an amount effective to activate the oxidative dye component;
   an effective amount of a thickening component in powdered form; and
   sucrose in powdered form, wherein the sucrose is present in the hair dye composition in an amount of approximately 30–65 weight percent, based on the total weight of the powdered hair dye composition, wherein said powdered hair dye composition is mixed with water before application to the hair.

2. A hair dye composition as in claim 1, wherein the oxidative dye component is at least one material selected from the group consisting of aromatic phenols, polycyclic phenols, and hydroxy benzene with at least one substitute group.

3. A hair dye composition as in claim 2, wherein the at least one substitute group is selected from the group consisting of nitro, amino, amido, sulfo, chloro, bromo, combinations thereof, and associated acid salts.

4. A hair dye composition as in claim 1, comprising approximately 4–13 percent by weight of the oxidative dye component, approximately 30–50 percent by weight of the oxidizing component, and approximately 2–3 percent by weight of the thickener component.

5. A hair dye composition as in claim 1, comprising approximately 42–45 percent by weight percent sodium peroxycarbonate; approximately 42–48 percent by weight sucrose, approximately 2–3 percent by weight xanthan gum, and approximately 4–13 percent by weight oxidative dye component.

6. A hair dye composition as in claim 1, further comprising a protein material.

7. A hair dye composition as in claim 1, further comprising water, wherein the composition includes approximately 4–6 parts water by weight for each 1 part of the powdered hair dye composition.

8. A hair dye composition as in claim 6, wherein the protein component is at least partly hydrolized.

9. A hair dye composition as in claim 6, wherein the protein component is a protein selected from the group consisting of keratin protein, collagen protein and amino acid hydrosolates.

10. A hair dye composition as in claim 6, comprising:
    approximately 4–13% by weight oxidative dye component;
    approximately 42–45% by weight oxidizing component;
    approximately 2–3% by weight thickening component; and
    approximately 1–3% by weight protein component.

11. The powdered hair dye composition of claim 1, wherein when mixed with water in a ratio of approximately 4–6 parts water for each 1 part of powdered hair dye composition, the resultant mixture has a pH in the range of 8 to 10.5.

12. A method for applying a hair dye to hair, comprising the steps of:
    providing a powdered hair dye composition;
    placing the powdered hair dye composition into a bottle so that the bottle is partially filled with the powdered hair dye composition;

placing a quantity of water into the bottle so that the bottle contains both the powdered hair dye composition and water;

mixing the powdered hair dye composition and the water inside of the bottle to form a liquid hair dye composition;

providing an applicator on the bottle, the applicator comprising a material through which the liquid hair dye composition may flow; and positioning the bottle so that the liquid hair dye composition flows through the applicator and contacts the hair wherein said powdered hair dye composition comprises:

an oxidative dye component in powdered form in an amount effective for coloring hair;

an oxidizing component in powdered form in an amount effective to activate the oxidative dye component;

an effective amount of a thickening component in powdered form; and sucrose in powdered form, wherein the sucrose is present in the hair dye composition in an amount of approximately 30–65 weight percent, based on the total weight of the powdered hair dye composition.

13. A method as in claim 12,:

wherein the applicator a valve stem with an integral spring and a cover; and pressing the applicator against the hair so that the integral spring is stressed and the liquid hair dye composition is passed through the cover to contact the hair.

14. A method as in claim 12, wherein the powdered hair dye composition comprises:

approximately 4–13 percent by weight oxidative dye component;

approximately 30–50 percent by weight oxidizing component;

approximately 1–4 percent by weight thickening component;

up to approximately 3 percent by weight protein component; and approximately 30–65 percent by weight sucrose.

15. A method as in claim 12, wherein the ratio of powdered dye composition to water in the bottle is in the range of about 1 part powdered dye composition to about 4–6 parts water.

16. A hair dye system comprising:

a powdered hair dye composition;

a bottle into which the powdered hair dye composition is disposed, the powdered hair dye composition only partially filling the bottle so that water may be added to the bottle and the contents mixed in the bottle to form a liquid hair dye composition; and an applicator comprising a material through which the liquid hair dye composition may flow out of the bottle and onto hair, wherein said powdered hair dye composition comprises:

an oxidative dye component in powdered form in an amount effective for coloring hair;

an oxidizing component in powdered form in an amount effective to activate the oxidative dye component;

an effective amount of a thickening component in powdered form; and sucrose in powdered form, wherein the sucrose is present in the hair dye composition in an amount of approximately 30–65 weight percent, based on the total weight of the powdered hair dye composition.

17. A hair dye system as in claim 16, wherein the applicator includes a valve stem with an integral spring and a cover material so that when the integral spring is stressed a liquid hair dye composition may pass through the cover.

18. A hair dye system as in claim 16, wherein the powdered hair dye composition comprises:

approximately 4–13 percent by weight oxidative dye component;

approximately 30–50 percent by weight oxidizing component;

approximately 1–4 percent by weight thickening component; and up to approximately 3 percent by weight protein component.

* * * * *